US012343151B2

(12) United States Patent
He et al.

(10) Patent No.: US 12,343,151 B2
(45) Date of Patent: Jul. 1, 2025

(54) METHODS AND APPARATUS FOR DETECTION AND IMAGING OF EPILEPTOGENICITY FROM SCALP HIGH-FREQUENCY OSCILLATIONS

(71) Applicant: CARNEGIE MELLON UNIVERSITY, Pittsburgh, PA (US)

(72) Inventors: Bin He, Pittsburgh, PA (US); Zhengxiang Cai, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 447 days.

(21) Appl. No.: 17/071,979

(22) Filed: Oct. 15, 2020

(65) Prior Publication Data

US 2021/0106247 A1   Apr. 15, 2021

Related U.S. Application Data

(60) Provisional application No. 62/973,625, filed on Oct. 15, 2019.

(51) Int. Cl.
*A61B 5/00* (2006.01)
*A61B 5/291* (2021.01)
*A61B 5/316* (2021.01)
*A61B 5/372* (2021.01)

(52) U.S. Cl.
CPC ............ *A61B 5/316* (2021.01); *A61B 5/291* (2021.01); *A61B 5/372* (2021.01); *A61B 5/4094* (2013.01); *A61B 5/6814* (2013.01); *A61B 5/7207* (2013.01); *A61B 5/7225* (2013.01); *A61B 5/7246* (2013.01); *A61B 5/7257* (2013.01)

(58) Field of Classification Search
None
See application file for complete search history.

(56) References Cited

U.S. PATENT DOCUMENTS

2012/0245481 A1* 9/2012 Blanco ................. A61B 5/7264
600/544
2018/0000370 A1* 1/2018 Modur ................. A61B 5/4094

FOREIGN PATENT DOCUMENTS

WO   WO-2018102815 A1 *  6/2018  ............. A61B 5/24
WO   WO-2018218174 A1 * 11/2018  ............. A61B 5/076

OTHER PUBLICATIONS

Chu et al. A semi-automated method for rapid detection of ripple events on interictal voltage discharges in the scalp electroencephalogram. Journal of Neuroscience Methods 277 (2017) 46-55. (Year: 2017).*
Jacobs et al. The identification of distinct high-frequency oscillations during spikes delineates the seizure onset zone better than high-frequency spectral power changes. Clinical Neurophsiology 127 (2016) 129-142. (Year: 2016).*

(Continued)

*Primary Examiner* — Etsub D Berhanu
(74) *Attorney, Agent, or Firm* — Michael G. Monyok

(57) ABSTRACT

A system and method to facilitate the analysis of long-term scalp EEG recordings and the investigation of underlying epileptogenicity. Pathological high frequency oscillations are identified and extracted from the EEG recordings and electrophysiological source imaging is used to reconstruct cortical activity, which can be used as an aid in surgical resection for the treatment of epilepsy.

18 Claims, 13 Drawing Sheets

(56) References Cited

OTHER PUBLICATIONS

Jacobs et al. High-frequency oscillations (HFOs) in clinical epilepsy. Progress in Neurobiology 98 (2012) 302-315. (Year: 2012).*

Bragin et al. Further evidence that pathologic high-frequency oscillations are bursts of poulation spikes derived from recordings of identified cells in dentate gyrus. Epilepsia, 52(1):45-52, 2011. (Year: 2011).*

Worrell et al. Recording and analysis techniques for high-frequency oscillations. Progress in Neurobiology 98 (2012) 265-278. (Year: 2012).*

Nonoda et al. Interictal high-frequency oscillations generated by seizure onset and eloquent areas may be differentially coupled with different slow waves. Clinical Neurophysiology 127 (2016) 2489-2499. (Year: 2016).*

Waldman et al. A method for the topographical identification and quantification of high frequency oscillations in intracranial electroencephalography recordings. Clinical Neurophysiology 129 (2018) 308-318. (Year: 2018).*

Lu, Y., et al. "Noninvasive imaging of the high frequency brain activity in focal epilepsy patients." IEEE Transactions on Biomedical Engineering 61, No. 6 (2014): 1660-1667.

Pascual-Marqui, R.D., Standardized low-resolution brain electromagnetic tomography (sLOREfA): technical details. Methods Find Exp Clin Pharmacol, 2002. 24 Suppl D: p. 5-12.

Lawson, C.L. and R.J. Hanson, Solving least squares problems. vol. 15. 1995: Siam.

Blanco, J.A., et al., Unsupervised classification of high-frequency oscillations in human neocortical epilepsy and control patients. J Neurophysiol, 2010. 104(5): p. 2900-12.

Gardner, A.B., et al., Human and automated detection of high-frequency oscillations in clinical intracranial EEG recordings. Clin Neurophysiol, 2007. 118(5): p. 11 34-43.

Liu, S., et al., Exploring the time-frequency content of high frequency oscillations for automated identification of seizure onset zone in epilepsy. J Neural Eng, 2016. 13(2): p. 026026.

Nikulin, V.V., G. Nolte, and G. Curio, A novel method for reliable and fast extraction of neuronal EEG/MEG oscillations on the basis of spatio-spectral decomposition. Neuroimage, 2011. 55(4): p. 1528-35.

Thorndike RL (1953) Who Belongs in the Family? Psychometrika 18(4):267-276.

Otsu N (1979) A threshold selection method from gray-level histograms. IEEE transactions on systems, man, and cybernetics 9(1):62-66.

Shi X, et al. (2015) Textural feature extraction based on time-frequency spectrograms of humans and vehicles. IET Radar, Sonar & Navigation9(9):1251-1259.

Tzallas AT, et al. (2009) Epileptic seizure detection in EEGs using time-frequency analysis. IEEE Trans Inf Technol Biomed 13(5):703-710.

* cited by examiner

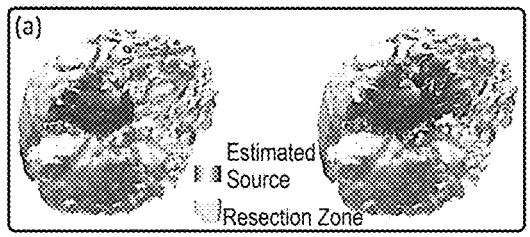
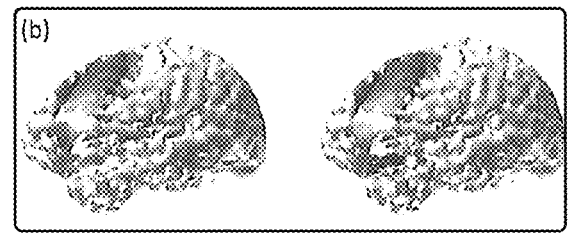
FIG. 6A                FIG. 6B
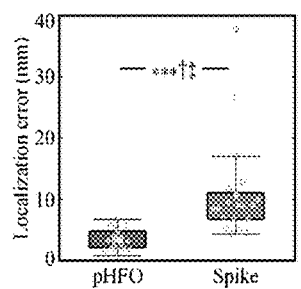
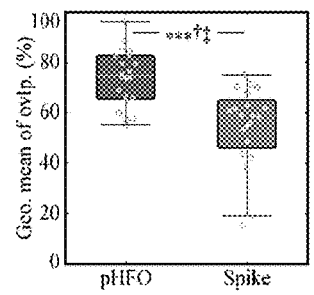
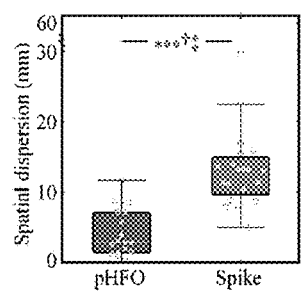
FIG. 6C        FIG. 6D        FIG. 6E
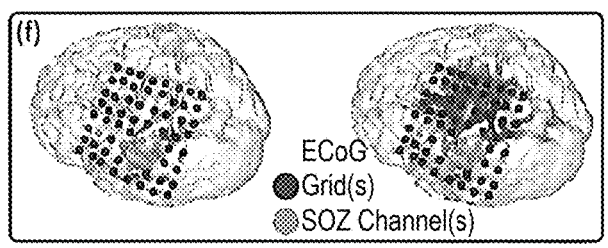
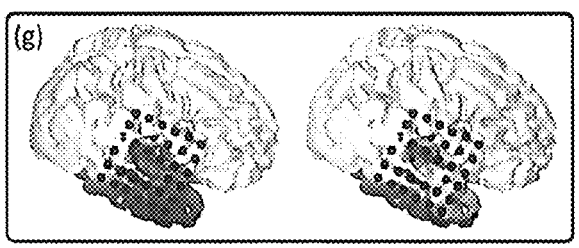
FIG. 6F                FIG. 6G

METHODS AND APPARATUS FOR DETECTION AND IMAGING OF EPILEPTOGENICITY FROM SCALP HIGH-FREQUENCY OSCILLATIONS

CROSS-REFERENCE TO RELATED APPLICATIONS

This application claims the benefit under 35 U.S.C. § 119 of Provisional Application Ser. No. 62/973,625, filed on Oct. 15, 2019, which is incorporated herein by reference.

STATEMENT REGARDING FEDERALLY SPONSORED RESEARCH

This invention was made with Government support under NS096761 awarded by the National Institutes of Health (NIH). The Government has certain rights in this invention.

BACKGROUND OF THE INVENTION

Epilepsy is one of the most common and severe chronic neurological disorder affecting approximately 65 million people in the world. Patients with epilepsy are usually treated with anti-epileptic drugs (AEDs) to suppress or prevent seizures with frequent mild-to-severe adverse effects; however, about 30% of the epilepsy patients do not respond to drug treatments. In such medically refractory epilepsy (MRE) patients, neurostimulation and resective surgery may be viable options to control or even stop seizures. Localizing the epileptogenic zone (EZ—the cortical area that is indispensable for seizure generation) is of great importance for guiding the brain stimulation or achieving postsurgical seizure freedom in resective surgery.

The last decades have observed numerous efforts in identifying the EZ, while it remains challenging even with all the combinations of diagnostic concepts and neurological modalities. In standard clinical trials, intra-cranial Electroencephalography (iEEG) using subdual grids, strips, and depth electrodes is the current gold standard of determining the seizure onset zone (SOZ, the cortical area where clinical seizures are generated), which might serve as an approximate of the EZ. However, iEEG is an invasive procedure, prone to induce various risks such as cerebral hemorrhage and infection and is also limited to regional coverage. As an alternative, scalp recorded Electroencephalography (EEG) is a noninvasive modality, which can be used to monitor and study the functional brain activities and pathological abnormalities via the electrophysiological source imaging (ESI) techniques. In this case, identifying an effective noninvasive biomarker of epileptogenicity could play a key role.

High-frequency oscillations (HFOs) are recorded electrical activities ranging from 80 to 500 Hz, including ripple (80-200 Hz), and fast ripple (200-500 Hz). During the last two decades, interictal HFOs have been observed in both local field potential and scalp EEG recordings as a potential biomarker of the pathological tissue in epilepsy to guide effective resective surgery and improve postsurgical outcomes. Studies have shown that HFOs are strongly correlated with the SOZ and the complete removal of brain areas with HFOs was found more likely to achieve a favorable surgical outcome. However, scalp HFOs, though promising in revealing the underlying epileptogenicity, are impeded from clinical translation and application by several challenges.

First, current identification of HFOs in scalp EEG is mainly based on manual labeling, which is tedious and laborious, and it is difficult to detect these low-amplitude and brief events in noisy EEG recordings automatically. Although there have been several automated detectors reported in iEEG studies, the development of such detectors is still deficient for noninvasive EEG recordings due to the high noise level and more artifacts in scalp EEG which might lead to low sensitivity or high false positive rates.

Second, there are insufficient evidences in the current detection techniques to distinguish pathological events from non-pathological events, especially from the physiological ones. Prior studies generally considered HFOs as events that standing out of the background activity in scalp EEG ranging in either 80-200 Hz or 200-500 Hz. However, recent research also reported ripple and fast ripple events existing in both epileptic and non-epileptic regions in human brain. Therefore, simple measures, such as frequency and amplitude, might not serve well the purpose of correctly discriminating the pathological HFOs. Stated differently, the presence of physiological high-frequency activities (HFAs), often sharing the same frequency band with the pathological HFOs, makes automatic distinction of clinically relevant HFOs complicated, which may even result in conflicting evidence of HFOs as a biomarker of epileptogenic brain.

Third, it is difficult to utilize HFOs in scalp EEG to monitor or delineate the underlying epileptogenicity due to the high noise level contaminating the high-frequency band which might lead ESI techniques to spurious cortical activities. Up till now, only few studies demonstrated the potential approach to image HFOs via ESI in EEG or MEG localizing the EZ, however these studies are either limited to manual identification of HFOs or validated in a small scale, and most of them were only able to provide qualitative imaging results such as the congruence with clinical information instead of a quantitative estimation of the EZ.

Therefore, it would be beneficial to develop a detector of high sensitivity and selectivity to facilitate the analysis of long-term scalp EEG recordings and the investigation of underlying epileptogenicity. Further, a systematic assemble of various features and evidences would help identify pathological events. Finally, a quantitative estimation of the EZ would be of great significance in clinical application to serve as a reference of pre-surgical guidance to surgery or brain stimulations.

BRIEF SUMMARY

According to embodiments of the present invention is a system and method for noninvasively delineating underlying epileptogenicity in a quantitative way via electrophysiological source imaging (ESI) with a process for identifying HFOs in scalp EEG recordings for patients with medical refractory epilepsy (MRE). One method comprises the detection, discrimination, extraction, and imaging of HFOs in scalp EEG for the purpose of revealing the underlying epileptic activity and localizing the potential EZ to provide insights for clinicians and facilitate clinical management of epilepsy in pre-surgical diagnosis and post-surgical evaluation.

In some embodiments, described herein includes the methods for detection, determination, extraction, and imaging of scalp recorded HFOs. In an alternative embodiment, the method comprises identification of HFOs cooccurring with spikes (a typical inter-ictal epileptiform discharge) from scalp recordings and utilizing such HFOs to noninvasively delineate the underlying epileptogenicity in human patients with MRE. In yet another alternative embodiment, the method comprises the detection, discrimination, extraction, and imaging HFOs from scalp recordings such as EEG or MEG.

BRIEF DESCRIPTION OF THE SEVERAL VIEWS OF THE DRAWINGS

FIGS. 6A-6J depict the results of electrophysiological source imaging, according to one embodiment.

DETAILED DESCRIPTION

Figure 1:
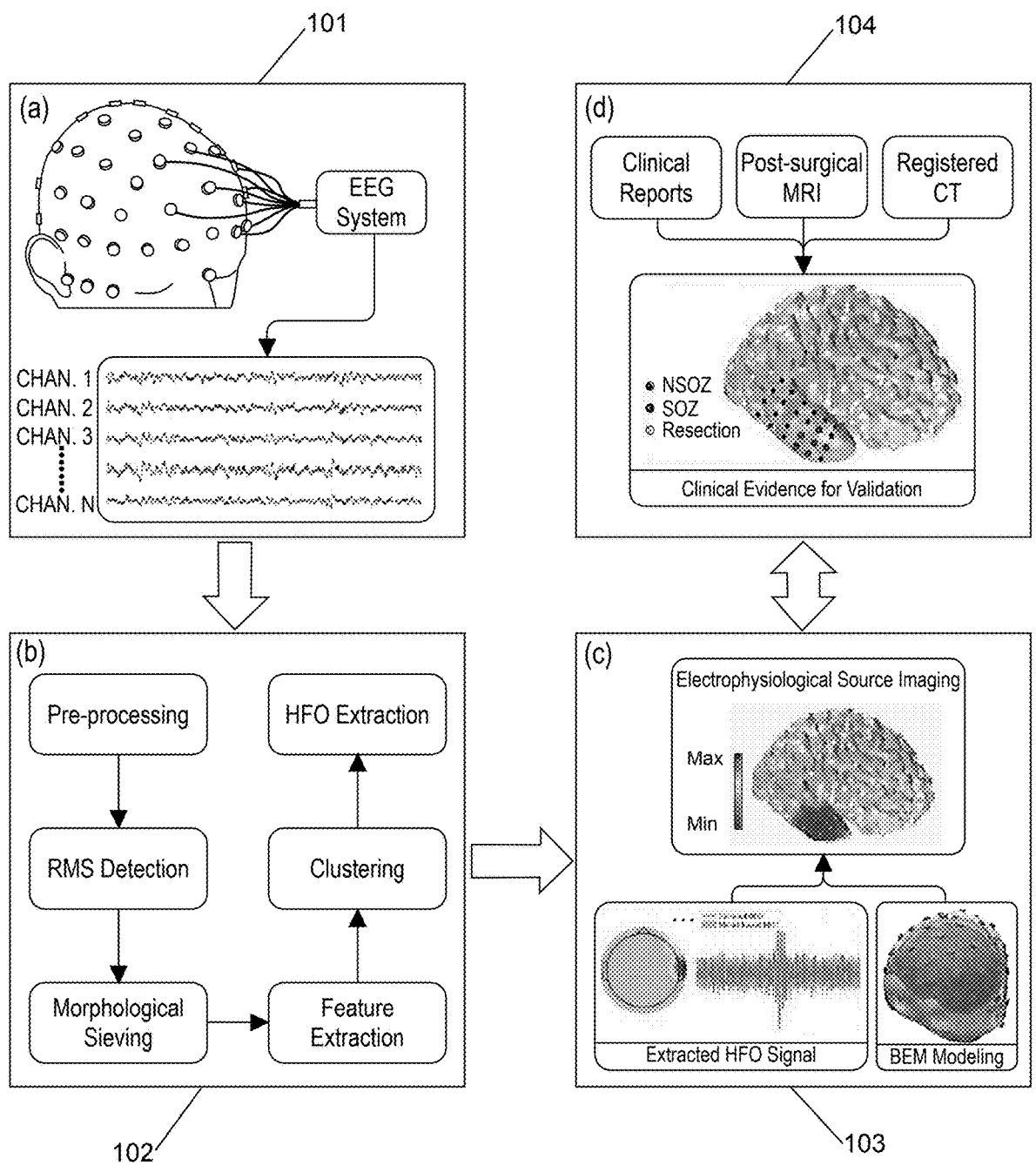
FIG. 1 is a flowchart of the method of detecting, determining, extracting, and imaging of scalp recorded high-frequency oscillations, according to one embodiment.

In epilepsy, high-frequency oscillations (HFOs) are observed and defined as events that stand out of the background with an approximately sinusoidal shape and a duration of at least four cycles. Studies have also observed nearly half of the ripples cooccurring with spikes (a typical form of inter-ictal epileptiform discharges, IEDs), termed "spike-ripples" (sRipples). These events are easier to detect than HFOs appearing alone and might be more related to pathological epileptic activities. Therefore, the method of the present invention, named Spike Ripple Source Imaging Algorithm (SPIRAL), can be used to detect, discriminate, and image the sRipples in scalp EEG for the purpose of delineating the epileptogenicity in epilepsy patients. A diagram of SPIRAL method is illustrated in FIG. 1.

The method consists of two major modules, namely, an identification module and an ESI module, which perform certain steps of the method. First, at step 101, scalp EEG data is recorded using a scalp EEG system. Then at step 102, signal processing is performed to reduce possible noise and artifacts existing in the data. During this step, the EEG data is scanned to discover all possible HFO events, and clusters all these events based on their unique features and find the most putative cluster of sRipples. As shown in FIG. 1, step 102 comprises the following sub-steps: step 111—pre-processing; step 112—RMS-detection; step 113—morphological sieving; step 114—feature extraction; step 115—clustering; and step 116—HFO extraction. Next, at step 103, the extracted sRipples are projected onto the cortex space to image the underlying epileptic activities. At step 104, the ESI results can then serve as a potential reference for presurgical diagnosis and/or post-surgical evaluation of patients with epilepsy, comparing to clinical evidences such as evaluation reports, resection zone derived from the post-surgical MRI, or SOZ localized from CT reregistered with MRI.

Figure 2:
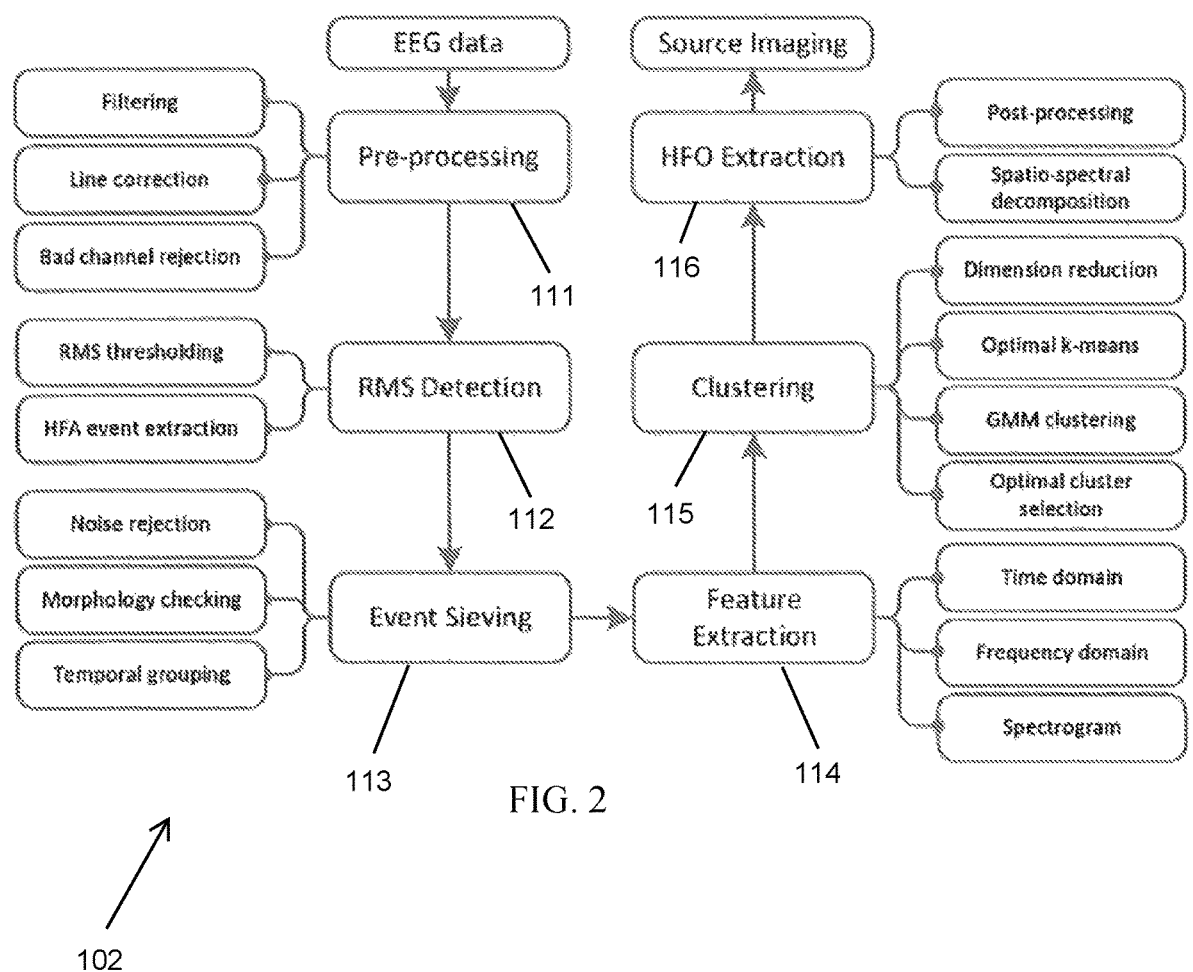
FIG. 2 is a diagram of the signal processing module.

FIG. 2 is a diagram of the imaging (or signal processing) module, which performs sub-steps 111-116. Specifically, signal processing comprises: EEG pre-processing at step 111 to eliminate as much noise and artifacts as possible; RMS detection at step 112 to sort out all possible high-frequency events; event sieving at step 113 to select only those events complying with the definition of HFOs determined by the clinician or based on current understandings; feature extraction at step 114 to setup the features used for clustering of the detected events; clustering at step 115 to select the most putative cluster of sRipples; and extraction at step 116 to get the multichannel HFO data for the ESI procedure. The sub-steps are discussed in further detail as follows.

EEG pre-processing—Raw EEG data are prone to contain artifacts generated by many physiological (cardiac pulse, respiratory, sweat, eye movement, muscle movement, etc.) and non-physiological (power line, bad recording channels, etc.) sources. Such artifacts and noise have to be carefully identified and removed from further analysis. To remove these artifacts, at step 102, the EEG data is first high-pass filtered above 1 Hz and notch filtered at 60 Hz with harmonics using an FFT Hann filter with a slope of 2 Hz (see FIG. 2). Next, the EEG data is reviewed to mark out the spikes existing in scalp EEG recordings and segmented into spike epochs. In one embodiment, each epoch can be set to 1 s in length and centered at the peak of the spike event. The epochs are also inspected to make sure that obvious artifacts were not included during the extracted interval and channels with suspicious noise are carefully interpolated with the surrounding good channels.

RMS detection—In the following process, as shown in FIG. 2, each channel of EEG data is processed individually. First, the segmented spike epochs were filtered above 80 Hz using a 64-order FIR filter in the forward and reverse directions to avoid phase distortion. In each channel of one spike epoch, the standard deviation (SD) is calculated for the high-pass filtered data using a 100 ms moving window with a 2 ms shift. The distribution of the calculated SDs is then modeled and an RMS threshold is set at three times the median of the SDs. All the samples with an amplitude exceeding this RMS threshold are first detected and samples which are within a 200 ms time window were grouped and compared to only include the sample with the maximum amplitude. An event epoch of 256 ms before and after each remaining sample is extracted from the unfiltered data (before 80 Hz high-pass filtering), representing one sample of high-frequency activity (HFA) for further processing.

Event sieving—The morphology of the extracted HFAs are then automatically examined based on the knowledge established in the current understanding of HFOs. First, the zero-crossing number of each unfiltered HFA is counted, and those events with counts larger than 10 were regarded as noise and excluded. Then, the remaining events are filtered above 80 Hz using the abovementioned FIR filter and passed through the Hilbert transform to compute the envelopes. The first and last 160 ms of the HFA are taken as the baseline, and an envelope threshold is computed as two times the median of the baseline envelope distribution. Each high-pass filtered HFA event is ensured to have at least 4 cycles of oscillations exceeding this threshold. Besides, within each spike epoch, if there exist multiple HFA events originating from different channels but locating within a 100 ms time window, then these events are grouped and compared to only keep the one with largest energy as the representative event. A step-wise procedure is illustrated in FIG. 2.

Feature extraction and classification—As shown in FIG. 2, to prepare for unsupervised clustering on the detected events, a set of features are selected to cover the whole time-frequency domain of the HFA events, including the time-frequency features and spectrogram features. The time-frequency features included mean, variance, skewness, median frequency, and spectral centroid of the events both before and after high-pass filtered above 80 Hz, and ratio between the power of the high (above 80 Hz) and the low frequency band (1-80 Hz). The spectrogram features included entropy, third-order moment of the histogram, directionality, and block-wise power of the whole spectrogram which is calculated using the short-time Fourier transform (STFT). To reduce the possible redundancy and computational load, the dimensionality of the feature set is reduced using the principal component analysis (PCA). In general, 95% of the total variance was kept constructing the new feature set.

In an alternative embodiment, features are extracted from the time-frequency representation of the detected high-frequency events in the raw (unfiltered) data to characterize the patterns of each event in both low and high frequency domain. The adopted features come from three categories: temporal, spectral, and spectrogram patterns. The temporal features, namely, mean, variance, skewness, line length, and global to average-peak ratio, are computed on both unfiltered and filtered (>80 Hz) signals. The mean, variance, and skewness describe the general characteristics in the shape of the time course for a detected event. The line length (LL) was computed as the average of the first-order derivative of a signal (Eq. S1), denoting the complexity within a time series. Similarly, the global to average-peak ratio (GAPR) is a measure of the signal power fluctuation, which was computed as the ratio between the global maximum value and the average of all other local peaks (Eq. S2). A large GAPR would indicate an abrupt jump in the signal peak relative to its background.

$$LL = \frac{1}{N} \sum_{i=1}^{N-1} |x(i+1) - x(i)| \quad (S1)$$

where x(i) is the $i^{th}$ element, and N is the length of the time series.

$$GAPR = \frac{g^*}{\frac{1}{l} \sum_{\{g_i \in G | g_i < g^*\}} g_i} \quad (S2)$$

where G is the set of all maxima in the time series, $g^*$=max G, and l is the number of all maxima that are strictly smaller than $g^*$.

The spectral features included median frequency, spectral centroid, and power band ratio. In detail, the median frequency was defined as the frequency at which the total power spectrum is divided into two equal areas. The spectral centroid (SC) was calculated as the weighted average of the frequencies in the spectrum of a signal with spectral magnitudes as the weights (Eq. S3), indicating the energy concentration of the spectrum of an event. These two measures were computed on both the filtered and unfiltered signals. The power band ratio was calculated as the power ratio of the high frequency band (>80 Hz) to the low frequency band (<80 Hz), which denotes the concentration of signal spectrum in high frequencies comped to low frequencies.

$$SC = \frac{\sum_{i=1}^{N/2} \frac{i}{NT} |X(i)|^2}{\sum_{i=1}^{N/2} |X(i)|^2} \quad (S3)$$

where T is the sampling period and X(i) is $i^{th}$ element in the Fourier transform of length N.

The spectrogram features were designed as the textural patterns of the spectrogram to capture the energy distribution in the time and frequency dimensions. The features included image entropy, third-order histogram moment, directionality, and block-wise power spectrum density. The image entropy (IE) measures the randomness of information in an image, characterizing the complexity of the texture in the spectrogram (Eq. S4). In general, the larger the entropy value, the more disordered the spectrogram is. The third-order histogram moment (THM) represents the symmetry of a statistical histogram, which denotes the amplitude fluctuation in a spectrogram (Eq. S5). The image directionality (ID) describes the direction in which the image texture concentrates or disperses. For this, the gradient vector at each pixel in a spectrogram was computed based on the horizontal and vertical gradients. Then, the amplitude and angle of the gradient vector were obtained as G and θ. By binning the gradient angle θ, the directionality histogram H was quantified by counting the number of pixels whose gradient amplitude in each angle bin exceeded the mean value of the amplitude. Subsequently, the peaks in the histogram H were located at angles of $\phi_p$ and the directionality was calculated as in Eq. S6. The block-wise PSD was computed as the sum of spectrum in non-overlapping time windows and frequency sub-bands. The spectrogram was equally divided into three temporal segments and the frequencies were binned into five bands: below 15, 15 to 30, 30 to 80, 80 to 150, and over 150 Hz, to capture the possible pathophysiological activities before, during, and after the detected events.

$$IE = -\sum_{i=1}^{N} p(i) \log(p(i)) \quad (S4)$$

where p(i) is the $i^{th}$ element in the normalized spectrogram energy distribution of length N.

$$THM = \sum_{i=1}^{N} (r_i - r_m)^3 f(r_i) \quad (S5)$$

where $r_i$ is the $i^{th}$ element in variable of the histogram with length N, $r_m$ is the mean value of the spectrogram, and f denotes the distribution of the statistical histogram for the spectrogram.

$$ID = \sum_{i=1}^{N_p} \sum_{j=1}^{N} (\phi(j) - \phi_p(i))^2 H(j) \quad (S6)$$

where is the binned gradient angle in the histogram, $\phi_p$ is the set of $N_p$ peaks in the histogram, and H is the distribution of the gradient histogram with length N.

Clustering—To partition the detected events into different groups according to the feature set extracted, the Gaussian Mixture Models (GMM) clustering is used. In GMM, the features are modeled as a mixed set of Gaussian distributions, and the method optimally fits the mean and variance of each Gaussian distribution. To initialize the GMM method, a k-means clustering is performed with an "elbow"

method to determine the optimal number of clusters and gives an initial estimation of the centers of the feature distributions. After the optimal number of clusters and the initial centers are found, the feature distributions are fine-tuned with the GMM to map each detected event into different groups using the expectation-maximization method.

To select the potential cluster of pathological HFOs (sRipples), two metrics, scalp spatial extent (SSE) and spike time-locking (STL), are calculated as reference to evaluate the homogeneity of the spatial and temporal distributions of all events clustered into each group.

$$SSE = \frac{\sum_{i \in I} \|s_i - \bar{s}\|_2}{N_I} \quad (1)$$

$$STL = \frac{\sum_{i \in I} |t_i - t_s|}{N_I} \quad (2)$$

where I is the set of events in one cluster, $s_i$ and $\bar{s}$ are the scalp location of event i and the averaged location of events in I, $t_i$, and $\bar{t}$ are the timing of event i and the nearest spike, and Ni is the number of events in this cluster. Based on the two metrics, the best potential pathological cluster is selected with the minimum mean of the two measures.

Multichannel sRipple extraction—After determining the potential cluster of sRipples, the multichannel epochs of sRipples after 80 Hz high-pass filtering are transferred into time-frequency spectrograms (TFS) using STFT. The power within each TFS map is examined to find the most prominent peak and the time and the frequency ranges of this main peak were estimated. After the estimation is done for each sRipple, the multichannel epochs are concatenated along the temporal dimension and passed through the spatio-spectral decomposition (SSD) method together with the estimated information of the time and the frequency ranges of the sRipple events. The SSD then provides a decomposition with which the original multichannel epochs could be separated into orthogonal temporal basis functions (see FIG. 3). The decomposed basis functions assemble the oscillatory activities specific at the presented time and frequency range with one topological scalp map paired with each temporal basis. Then the optimal number of basis functions to keep for reconstruction is determined based on the generalized eigenvalues estimated by SSD using the interquartile range (IQR) method. By projecting the remaining basis back to the original multichannel epoch domain, the "denoised" sRipple epochs can be extracted out from the noisy EEG signals.

Figure 3:
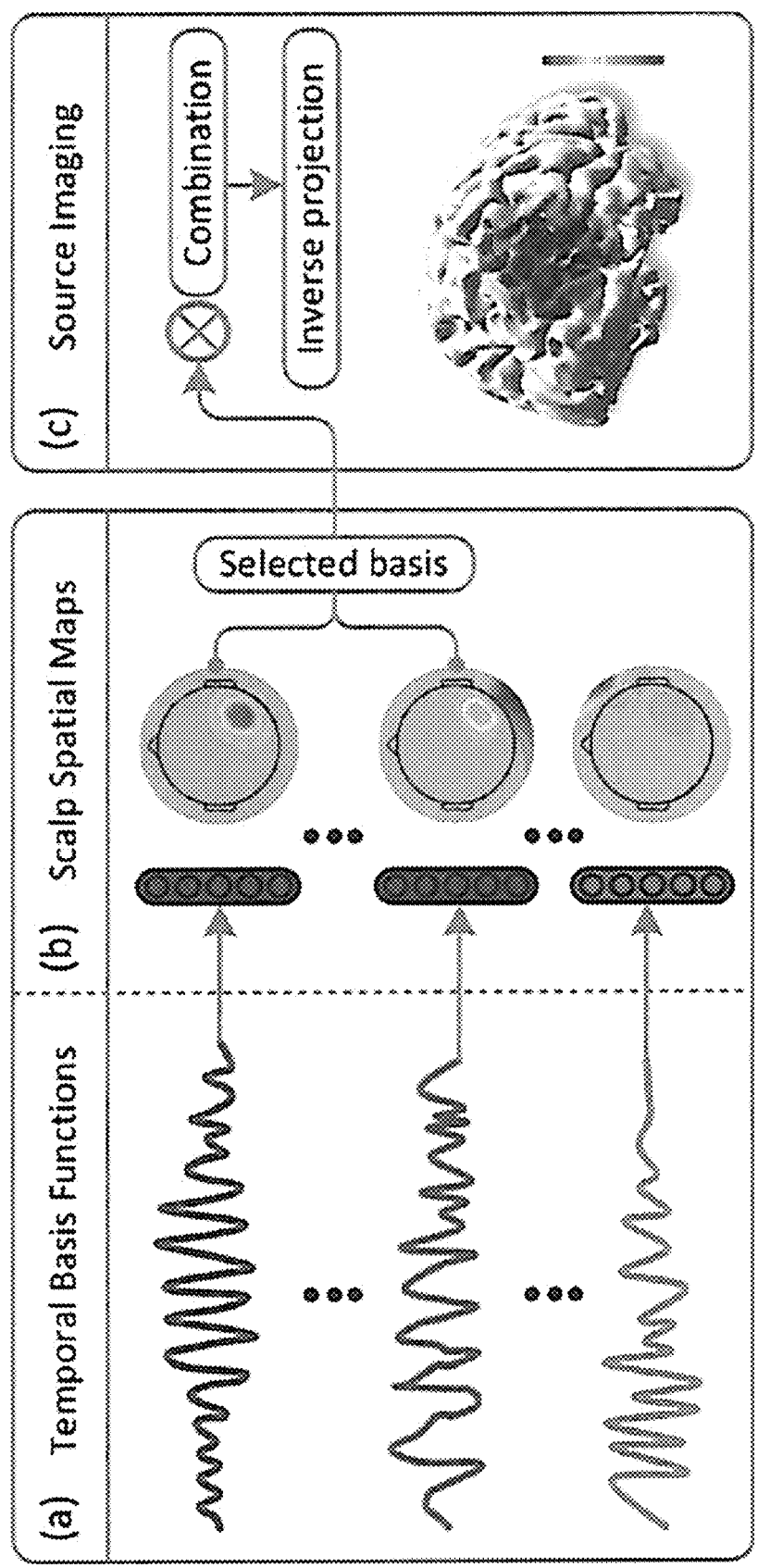
FIG. 3 is a diagram of the electrophysiological source image process, according to one embodiment.

As shown in FIG. 3, representations of temporal basis functions are generated from the SSD algorithm, and the scalp map of each basis function is shown with a representation of electrodes of each map. The selected temporal basis functions are projected through the spatial maps back to the original data space and combined as the "denoised" sRipple epochs. The inverse projection of the reconstructed sRipples presents the potential cortical activity underlying.

Electrophysiological source imaging (ESI)—Following the extraction of the sRipples, at step 103, ESI is performed on the extracted and denoised sRipples to reconstruct the cortical activity underlying. In ESI, it is assumed that the brain electrical activity can be modeled by current dipole distributions, and ESI estimates the neural electrical activity by projecting the scalp EEG measurements through the inverse operation of the lead-field matrix which represents the linear relationship between the cortical activity and the EEG measurement. The lead-field matrix can be constituted by the Maxwell's equations. The source space (brain cortex model) is discretized into a few thousands of evenly distributed regions within each of which a current dipole located at the center and by numerically solving the Maxwell's equations, a linear relationship can be derived as follows:

$$\varphi = Kj + n_0 \quad (3)$$

where $\varphi$ is the scalp EEG measurements (M×1), K is the lead field matrix (M×N) which can be numerically computed using the linear mapping between the source distribution and the scalp EEG based on the boundary element model (BEM), the current dipole distribution to be estimated is denoted by j (N×1), and $\eta_o$ is the additive noise in sensor space (M×1). The regarding source distribution can be estimated from the scalp EEG measurements by solving an inverse problem:

$$j = K^\dagger \varphi \quad (4)$$

where $K^\dagger$ is a general form of pseudoinverse of the lead field matrix. Many established methods can be used to solve this inverse projection problem. There is no particular restrictions in this application; one of the classical methods, standardized low-resolution brain electromagnetic tomography (sLORETA), is integrated.

As described previously, the sRipple activity is extracted from the noisy scalp EEG through SSD method which is a linear dimensionality reduction method, tailored for oscillatory signal analysis. With SSD, the scalp EEG measurements are projected into a lower dimensional space by a linear projection, and then transferred back to its original space to achieve a "denoised" low-rank factorization:

$$\check{\varphi}(t) A W^T \varphi(t) = \sum_{i=1}^{K} \alpha_i b_i s_i(t) \quad (5)$$

where: $\bar{\varphi}(t) \in \mathbb{R}^{M \times T}$ is the "denoised" sensor measurement, $A \in \mathbb{R}^{M \times K}$ is the activation pattern—spatial topo-maps—corresponding to the extraction filter $W \in \mathbb{R}^{M \times K}$, $\alpha_i \in \mathbb{R}^{M \times 1}$, $\alpha_i \in \mathbb{R}^{M \times 1}$ is one activation vector, $b_i \in \mathbb{R}$ is the weighting factor of each activation pattern, and $s_i(t) \in \mathbb{R}^{1 \times T}$ is the corresponding temporal pattern. Substituting Eq. (5) into Eq. (4), the source distribution estimation can be rewritten as:

$$\hat{j} = K^\dagger \bar{\varphi} = K^\dagger \sum_{i=1}^{K} a_i b_i s_i(t) = \sum_{i=1}^{K} (K^\dagger a_i) b_i s_i(t) = \sum_{i=1}^{K} \hat{j}_i b_i s_i(t) \quad (6)$$

where $\hat{j}, \hat{j}_i$ are the estimated source distribution of the "denoised" EEG measurements and each temporal activation component, respectively. By accomplishing all the above-mentioned procedures, the underlying cortical activity of the sRipples can be derived and potentially used as reference for further pre-surgical diagnosis or post-surgical evaluation.

Evaluation a) Simulations

To evaluate the method of the present invention, a large-scale Monte Carlo simulation was done using realistic EEG signals and brain models derived from real clinical data. The focus of the simulation was to validate the efficacy of the proposed method in detection and discrimination of the putative sRipples with repetitive morphology from the other HFA events such as artifacts and noise. To generate realistic simulation scenarios, the MRI images were collected from a human subject and a three-layer BEM model was derived to solve the forward problem and obtain the lead-field matrix, which maps the current dipole distribution on the cortex to the scalp EEG potentials.

Various EEG events that were typically observed in real recordings—spike, sRipple, and transient artifact which could lead to spurious HFOs—were modeled. In total, 100 cortical locations were randomly generated and 100 randomly selected event types (spike with/without HFOs) were distributed to each simulated location on the forward cortex model and then projected to the scalp to generate EEG measurements through lead-field matrix. For each cortical location, transient artifacts and four different kind of noise were added to the simulated EEG data, namely white Gaussian noise (WGN) at SNR of 20 dB, 10 dB, and 5 dB and realistic EEG background (BKG) noise at SNR of 5 dB.

As described previously, the algorithm first detects all possible events in a high sensitivity fashion, and then discriminates those putative sRipples via clustering method. As a result, the detected events were labelled as positive HFOs (pHFOs—putative sRipples) and false HFOs (fHFOs—the other events). To quantify the performance of the algorithm, detection sensitivity (recall), positive predictive value (precision), and F1 score (harmonic mean of the recall and precision) were calculated comparing the automatically determined sRipples to the manually labelled results across different noise levels.

Figure 4A:
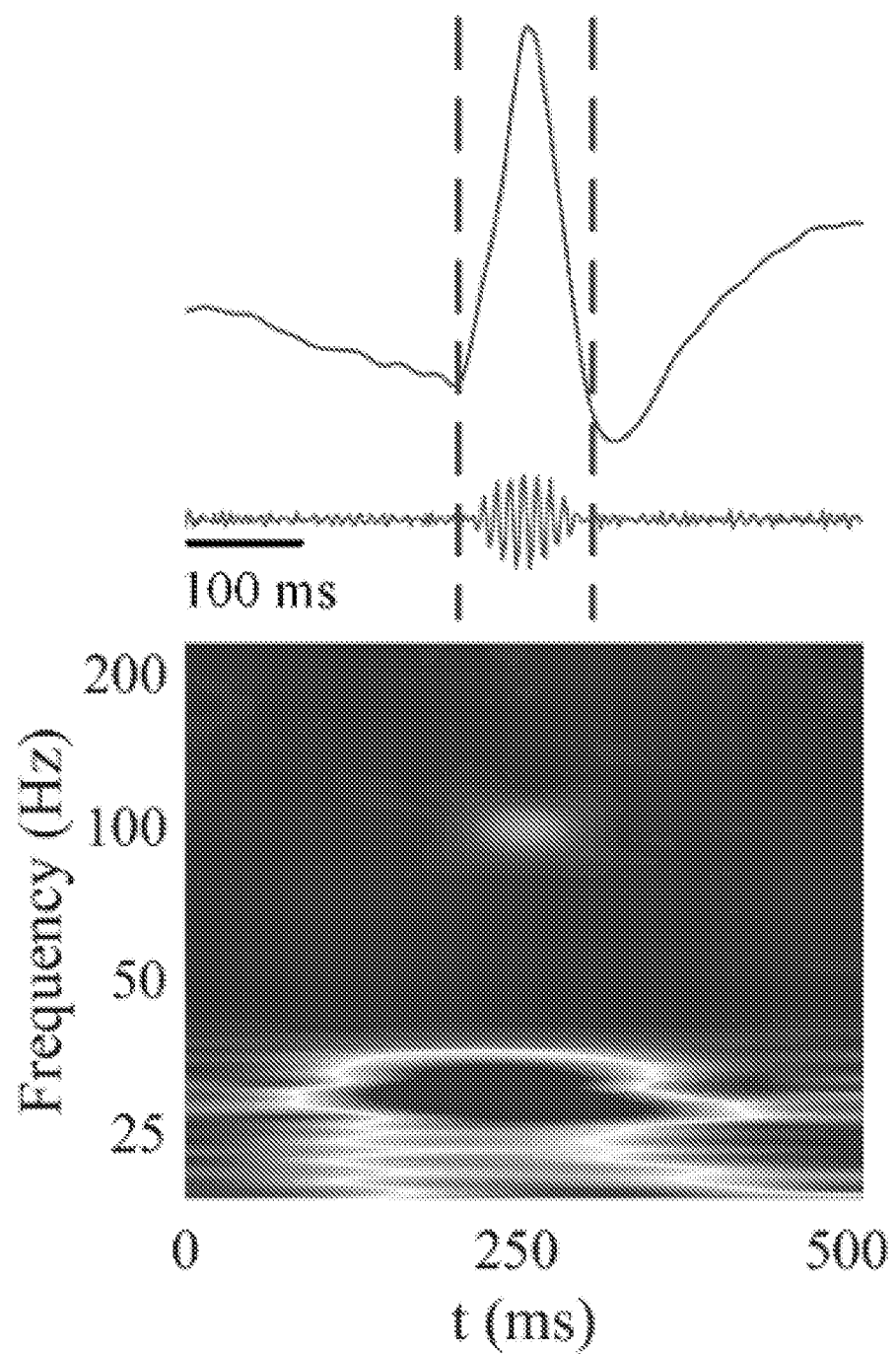
FIGS. 4A-4G depict detection and discrimination results of the method, according to one embodiment.
Figure 4B:
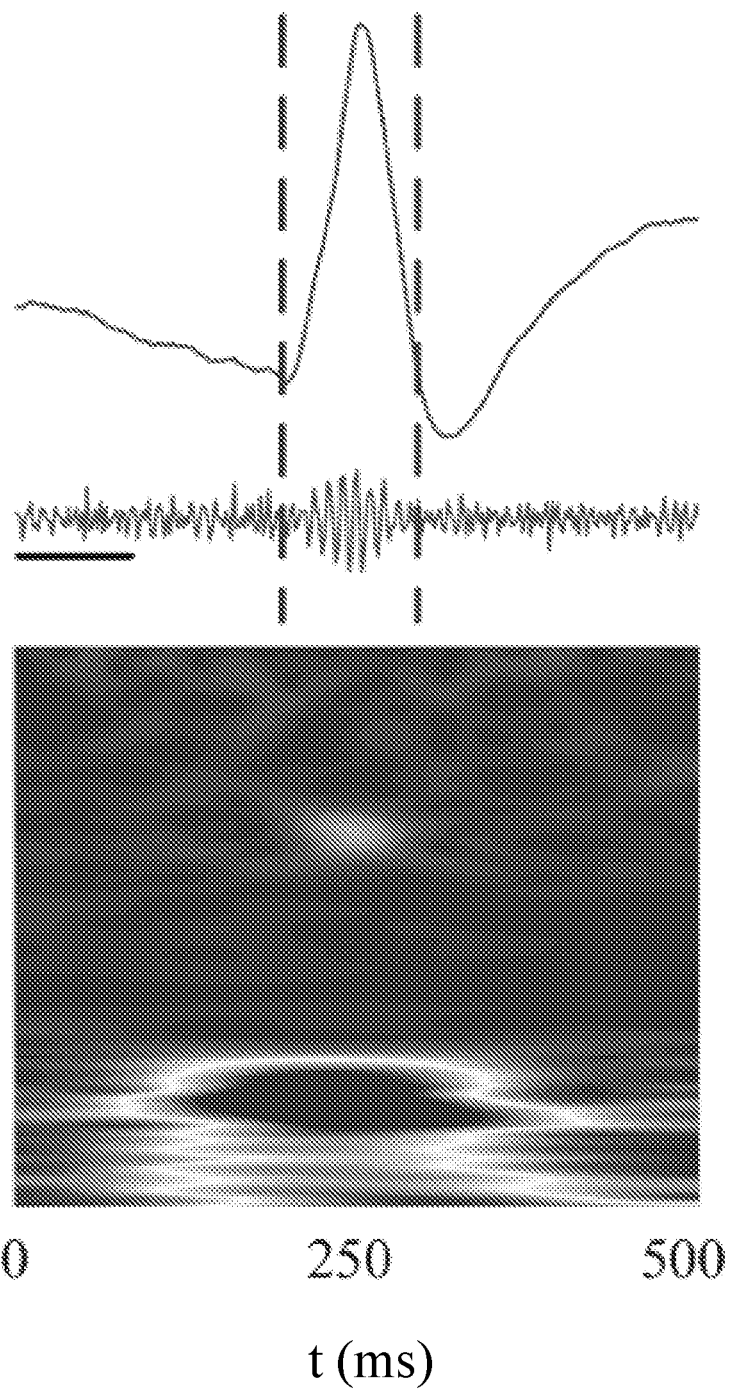
Figure 4C:
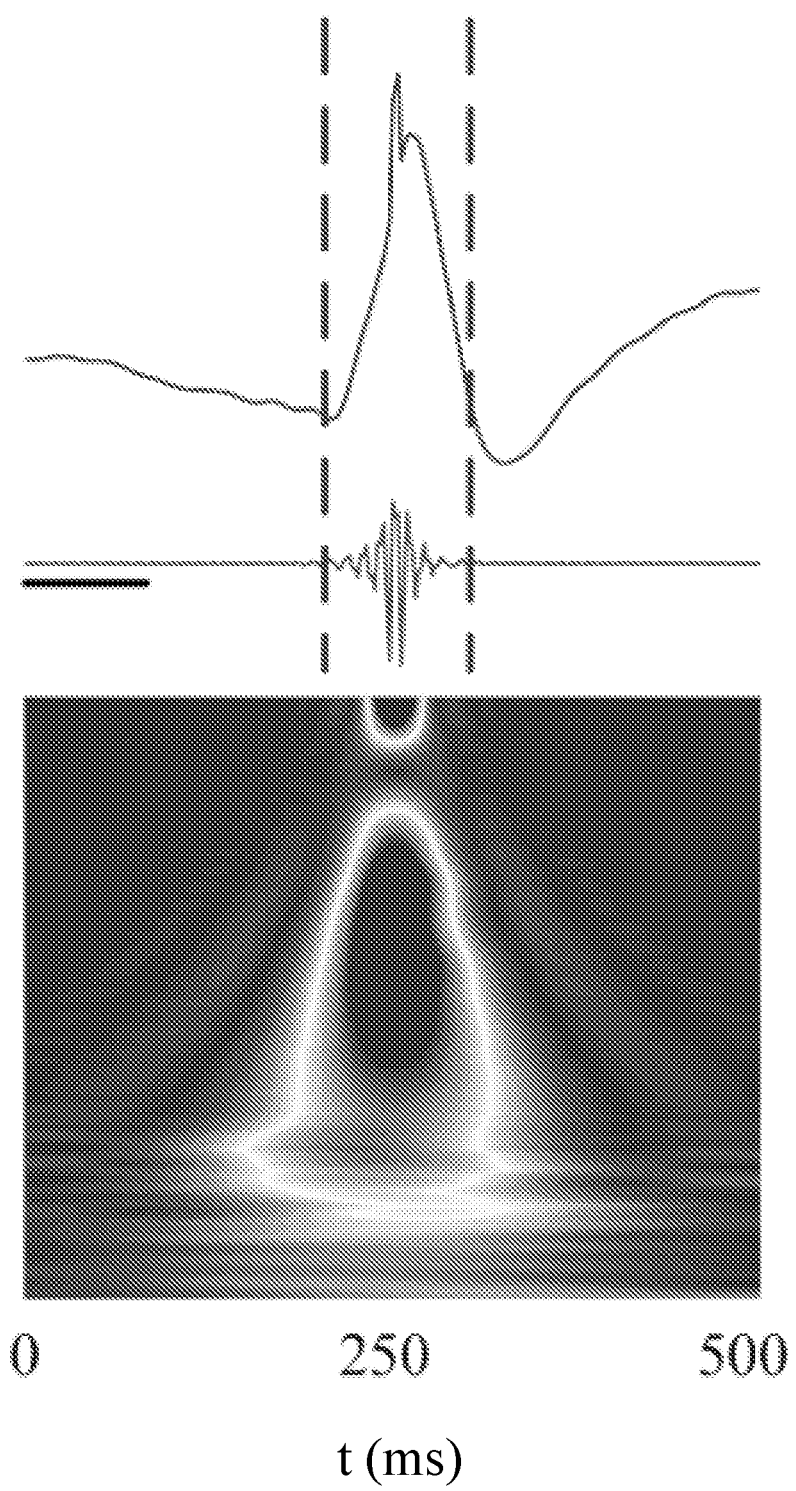
Figure 4D:
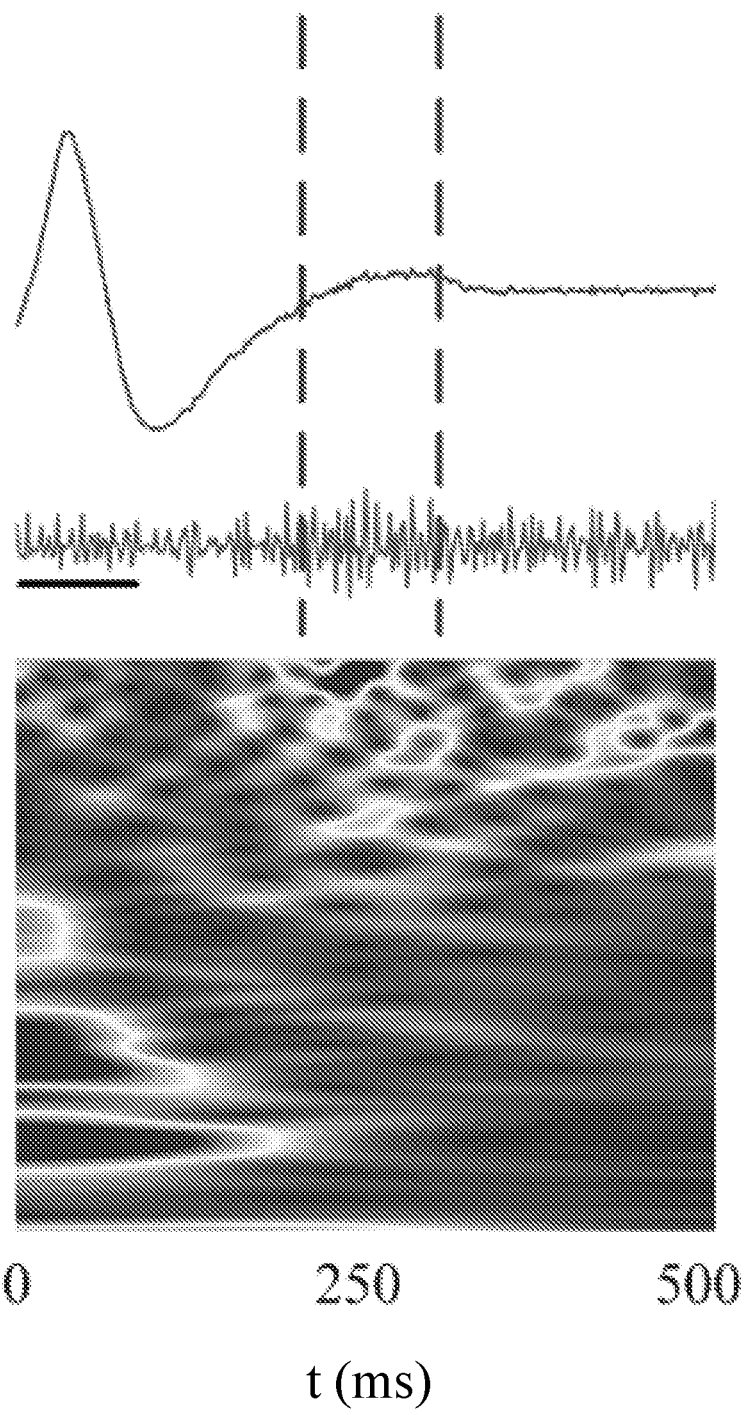
Figure 4E:
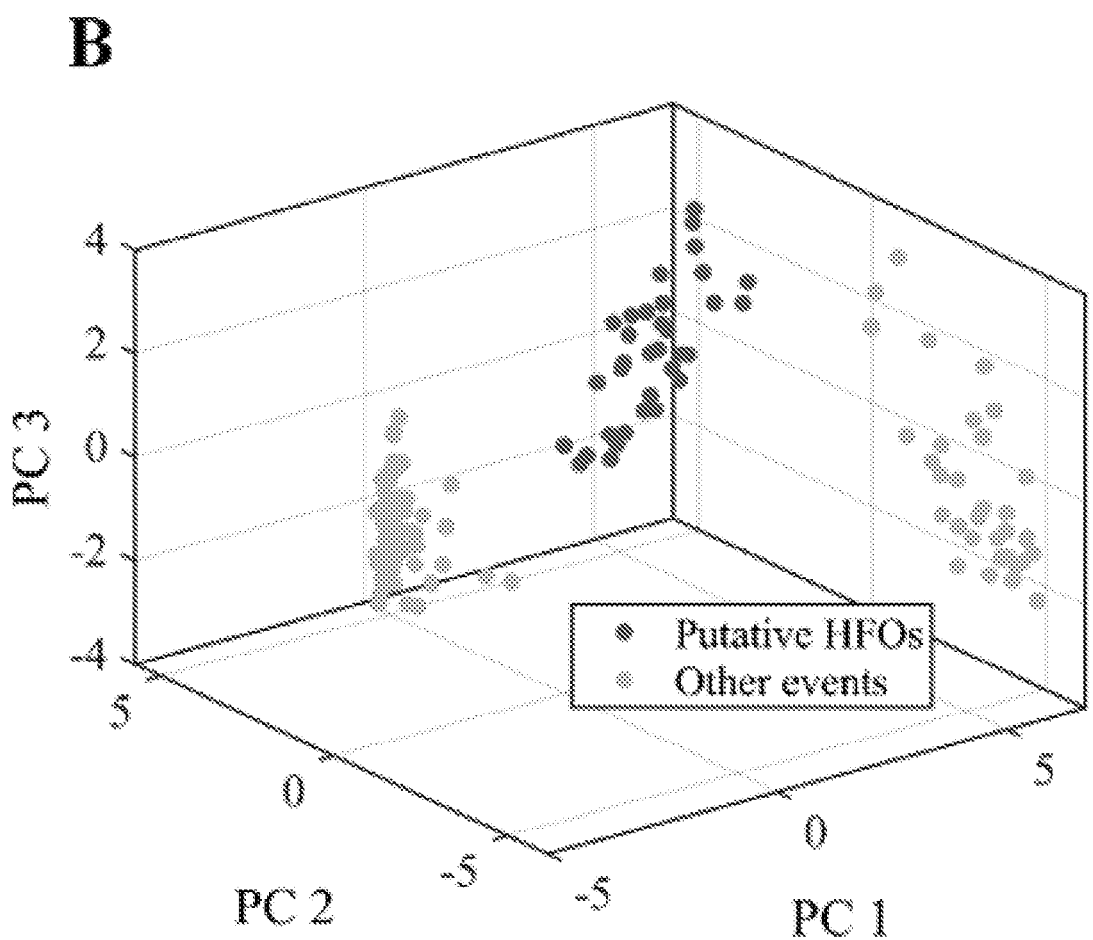
Figure 4F:
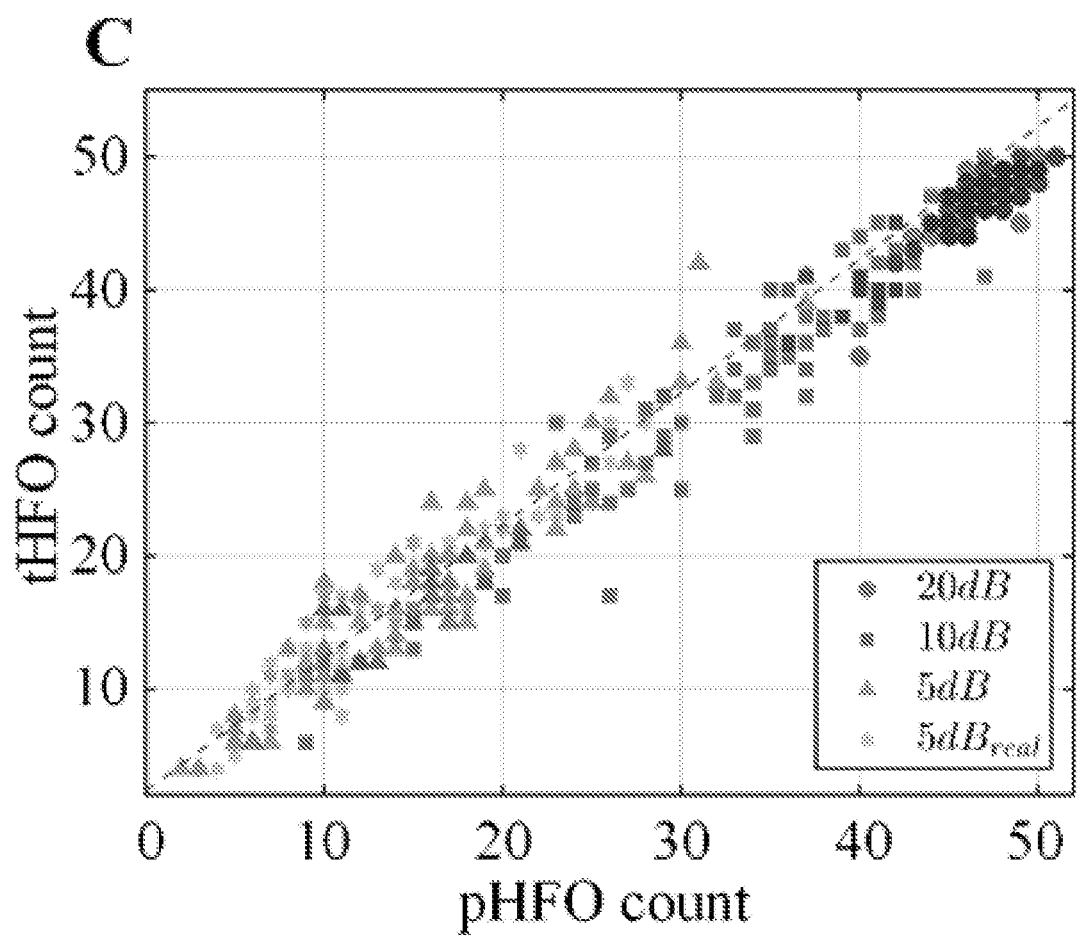
Figure 4G:
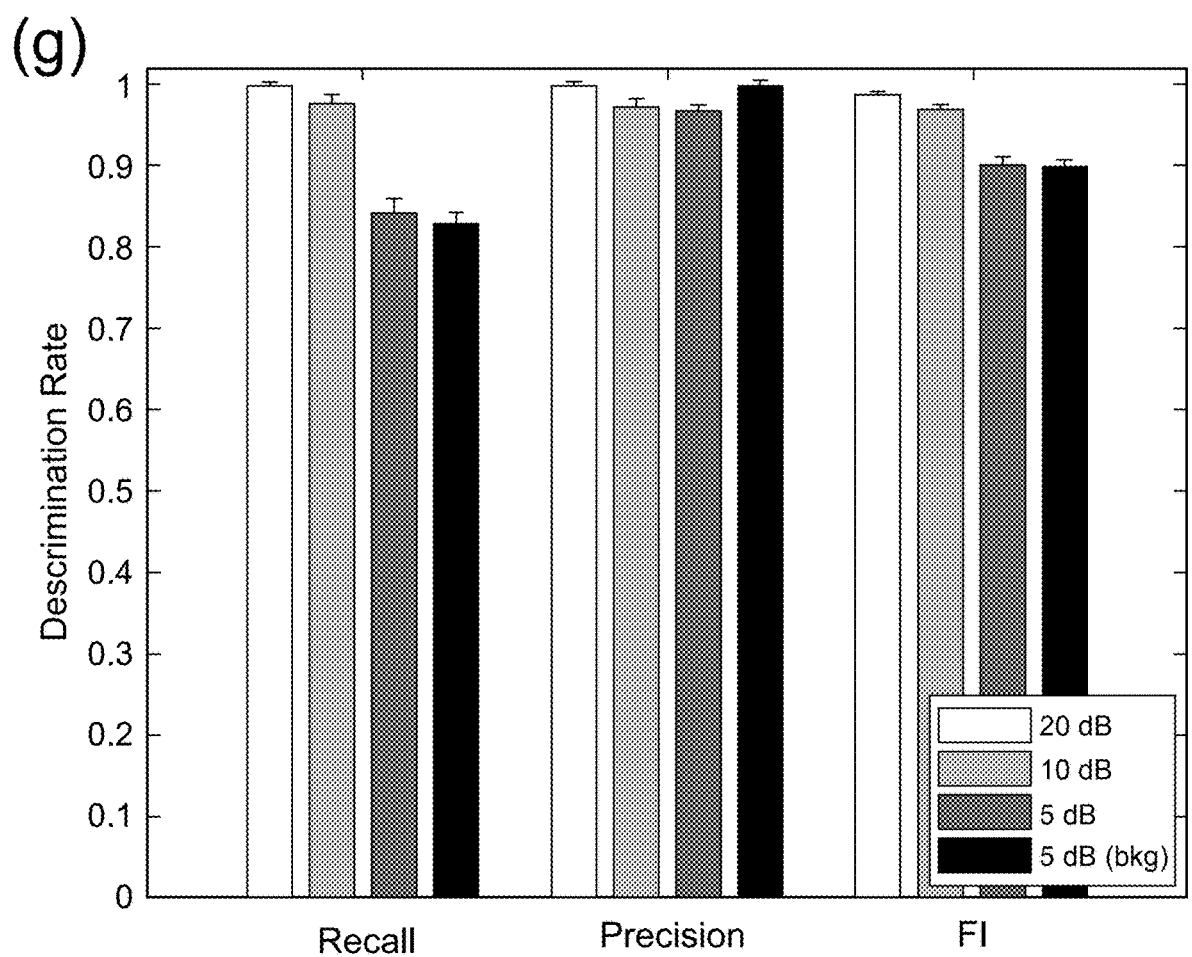

As shown in FIGS. 4A-4D, the method robustly detected the HFAs embedded in the noisy EEG data. By clustering the features extracted from each detected event, the method could well divide these events into several groups; each group represented one type of event. The putative sRipples were well separated from the other events such as noise and artifacts in the multi-dimensional feature space, which was demonstrated as a 3-dimensional feature space consists of the first three principle components of the feature set (FIG. 4E). Within each simulated location under a particular noise level, the number of the automatically determined sRipples (pHFOs) were compared to the number of tHFOs from human labeling. As shown in FIG. 4F, the two amounts were comparable to each other, and fitted to a straight line with a slop of 1.02 and $r^2$=0.91, representing a good match between these two variables. It should also be noted that the number of both detection and manual labeling went down simultaneously when the noise level increased (lower SNR), which means that at high noise level, it would be equally difficult for both human and the method to discover putative sRipples. Comparing the detection results in terms of recall, precision, and F1 score, as indicated in FIG. 4G, although the general performance went down when the noise level was high, the general performance was still good and robust. Even under the most severe noise levels, i.e., 5 dB white and realistic noise, the minimum of the median of recall was still above 80%, precision above 90%, and F1 score around 90%, which indicated the efficacy of the proposed algorithm under high level of noise.

Referring again to FIGS. 4A-4D, examples of detected HFA events are shown. Each figure displays the unfiltered EEG data (top line), the high-pass filtered EED data (above 80 Hz, bottom line), and the spectrogram of the unfiltered EEG data. An interval is labeled out surrounding the HFA (dashed line) on both the unfiltered and filtered EEG time course. The examples illustrate a sRipple event in low noise (20 dB SNR) (FIG. 4A), sRipple event in high noise (10 dB SNR) (FIG. 4B), spike with transient artifact whose high-frequency component might resemble sRipple event (FIG. 4C), and high frequency random noise (FIG. 4D). The detected events were clustered into different groups based on the features derived from the time-frequency domain, with the selected group as putative sRipples (pHFOs) and the other events as random noise or artifacts. The axes consist of the first three principle components of the feature space. (see FIG. 4E). The number of automatically determined sRipples is compared to that of the manual labels for each case. Each marker represents one case in the simulation and the overall relationship is fitted to a straight line (dashed line). (see FIG. 4F). FIG. 4G depicts the overall performance (recall, precision, and F1 score) of the method under four noise scenarios.

b) Clinical Study

To further test the application value of the method, according to one embodiment, a clinical study was designed to apply this method in a cohort of 29 patients with MRE. The main purpose of this study was to utilize the method, according to one embodiment, to identify sRipples in the scalp EEG of each patient and then image the underlying epileptic activity. The source imaging results were compared to the clinical evidences derived from the clinical reports and pre-surgical CT and/or post-surgical MRI. To further validate the value of clinical application for the proposed approach, traditionally established spike imaging approach, which utilizes spikes to do ESI and localize the EZ, were also implemented and compared to the clinical evidences.

The EEG recordings of each patient were first inspected to label and extract spike epochs, and then the segmented spike epochs were passed through the SPIRAL approach and the spike imaging approach to get the source imaging results as the estimations of EZ. For each patient, an individual brain model was made using the pre-surgical MRI. If the pre-surgical CT was available, the SOZ electrodes were co-registered onto the cortex model which was derived from the pre-surgical MRI. In another case, if the post-surgical MRI was available, the surgical resection area was marked and projected onto the cortex model. In some cases, the clinical reports might record the extract location of the SOZ electrodes and/or the resection region, and in these cases this information was also used as reference. Either SOZ location or resection area was used as the clinical evidence for later evaluation of the source imaging results.

A total of 29 patients were included in this validation study. All these patients had inter-ictal spikes recorded pre-surgically with high-density EEG (76 electrodes). The outcome of the surgical intervention was scored based on the international league against epilepsy (ILAE) system by the physicians. Among all patients, 21 patients were scored as ILAE 1-2 (no seizures), and 8 were scored ILAE 3-6 (non-seizure-free) during the follow-up period. The surgical resection area was available in 26 patients, which was extracted from the post-surgical MRI or clinical reports which might indicate the clear location and dimension of the resected region. In 11 patients, intra-cranial electrode locations were available from CT images and/or clinical reports. The SOZ location was determined based on the iEEG studies in these patients.

According to a method of one embodiment, for each patient included in this study, the EEG data was first band-pass filtered between 1-35 Hz and the primary and clear spikes were marked. Each spike was marked at the peak, which was regarded as the time zero of the spike epoch. It was ensured that no obvious artifacts or other events existing around within the period of ±500 ms from the marked peak. This interval was later extracted for each spike with each patient. In the cases that one patient had multiple types of spikes, the spike epochs were separated according to different spike types. Thus, each spike type could be separately processed by the spike imaging method, and the imaging results were averaged for comparison. However, in this embodiment, the spike epochs of different types of each patient were processed together. The output of SPIRAL and spike imaging was the estimated source activity of EZ for each patient. The imaging result was then compared to resection area and/or SOZ electrodes to calculate quantitative evaluation metrics.

For quantitative evaluation of the ESI results produced by SPIRAL and spike imaging, several widely used metrics were adopted here (1) averaged localization error (LE), (2) overlap rate, and (3) spatial dispersion (SD). The LE was defined as the average of the minimum pairwise distance between the estimation and the ground truth (resection or SOZ). To define the overlap rate, the overlap between the estimated source and the ground truth was first calculated and then normalized by either the area of ground truth and estimation, representing the recall and precision of the estimation comparing to the clinical evidence. The overlap rate ranges from 0 (no overlap) to 1 (perfect match). The SD was calculated as the weighted quadratic mean of the minimum pairwise distance between the estimation and the ground truth, characterizing the spatial spread of the estimated source.

Evaluation Results

Figures 5A, 5B, 5C:
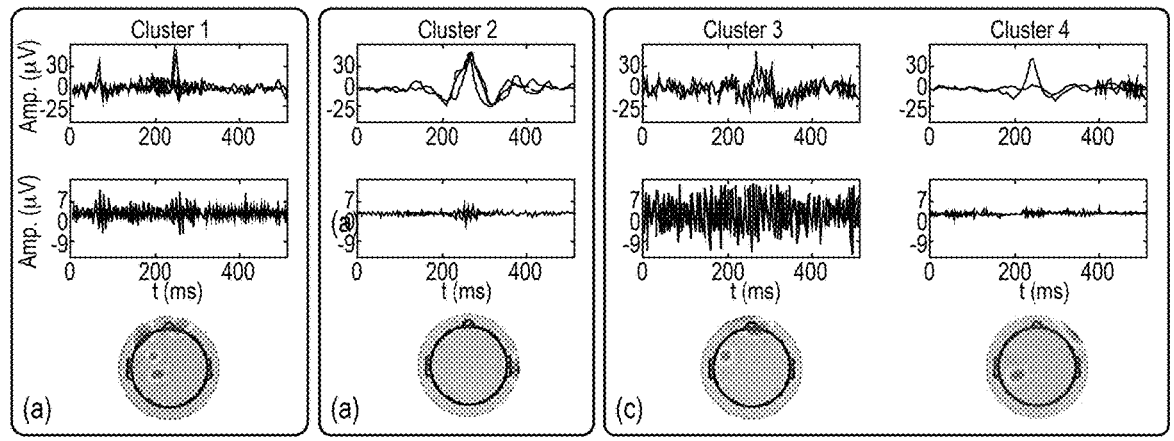
FIGS. 5A-5F are representative results of detection and clustering of events in the EEG data.
Figures 5D, 5E, 5F:
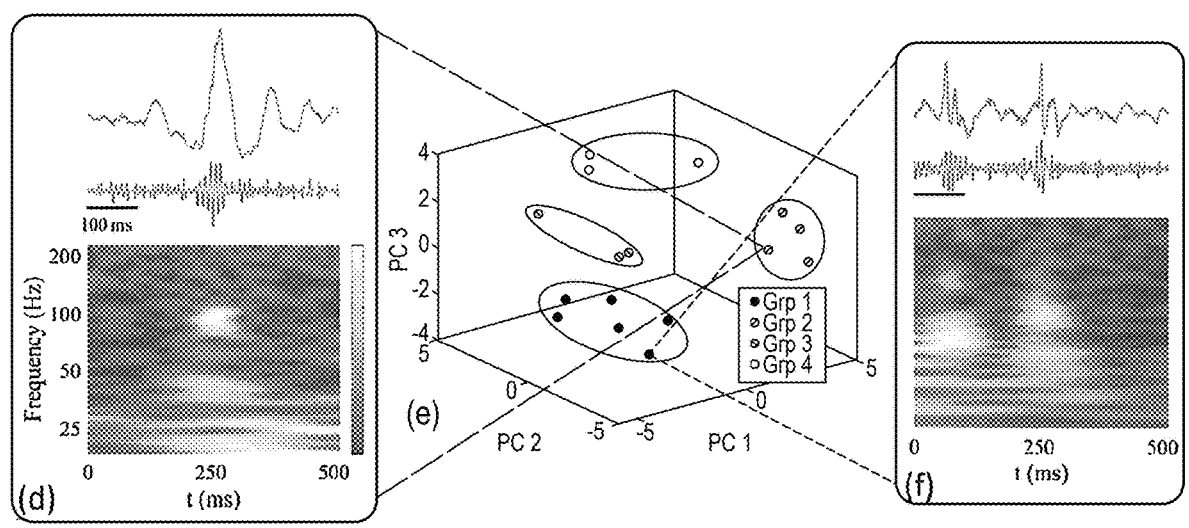
Figure 6H:
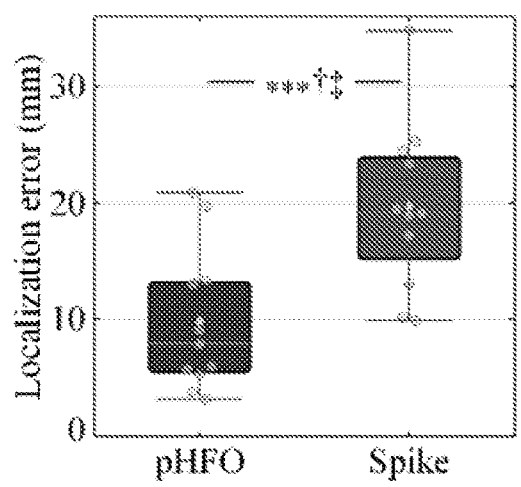
Figure 6I:
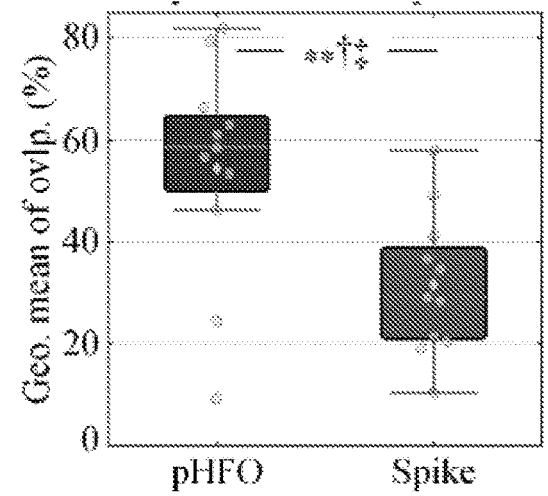
Figure 6J:
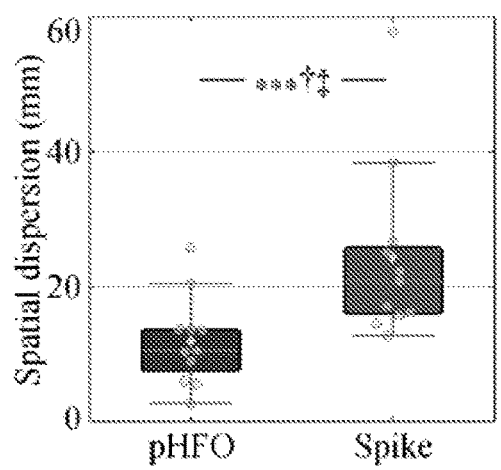

In the clinical dataset, various HFA events were observed and detected by the SPIRAL approach. FIGS. 5A-5F are representative results of detection and clustering in the clinical validation. In FIGS. 5A-5C, clusters of detected HFA events are shown, with the unfiltered time course (upper), the filtered time course (middle), and the scalp channel distribution of these events (lower). The cluster 2 (FIG. 5B) was selected based on the metrics SSE and STL, and the other clusters (FIG. 5A and FIG. 5C) were determined as artifacts or noisy events. The clustered events are also shown in the first three principle-component space of the feature set (FIG. 5E), with the selected cluster circled and shaded. Two examples represent the typical sRipple (pHFO) (FIG. 5D) and the artifact event (fHFO) (FIG. 5F). The time courses of the unfiltered (upper line) and the filtered EEG data (middle) and the spectrogram of the unfiltered EEG data (lower) are shown.

As shown in FIGS. 5A-5F, detected events can be separated into several clusters (FIG. 5E) and based on the metrics SSE and STL (Eq. (1-2)), the putative cluster of sRipples (pHFOs) can be selected, which was Cluster 2 in this case (FIG. 5E, marked), while the other clusters were categorized as nHFOs (FIG. 5E). The unfiltered and filtered waveform of the events in different clusters was distinct (FIGS. 5A-5C). Comparing the Cluster 2 to the other clusters, the unfiltered waveform of the events in Cluster 2 illustrated typical spike wave shape, and the filtered waveform demonstrated strong and clear oscillatory morphology (FIGS. 5A-5C). From the spectrogram of the two examples, one sRipple and one artifact event, it can also be noted that the sRipples (FIG. 5D) generally have a clearer separation between the low-frequency activity and the high-frequency oscillation comparing to the sharp-wave-induced artifacts (FIG. 5F).

After the selection of the putative sRipple cluster, the multichannel scalp activity was extracted from noisy epochs of the detected sRipples events. The extracted epochs were then averaged to get a representative scalp topographical map for further ESI analysis. The spike imaging was also conducted on the averaged spike epochs extracted from the EEG data for each patient for comparison. FIGS. 6A-6J depict the ESI results of sRipples and spikes validated with resection and SOZ. The ESI results validated with resection are shown in FIGS. 6A-6E.

As shown in FIGS. 6A-6E, the imaging results, validated with resection zone, indicate that in this cohort of patients the LE using sRipples (or pHFOs) was around 4.6 ($\pm$3.32 STD) mm comparing to 11.8 ($\pm$7.59) mm using interictal spikes, and the LE of sRipples was significantly lower than that of spikes ($p<0.001$; Cohen's $d>0.8$). The averaged overlap rate of sRipples was 72% ($\pm$15.58%) comparing to 53% ($\pm$15.31%) of spike imaging, which indicated that the estimated sources of sRipples in general have a better coverage of the surgical resection comparing to interictal spikes which are more spread in terms of cortical activation in our tested cohort ($p<0.001$, Cohen's $d>0.8$). Similarly, the SD also indicated that the ESI results of sRipples were more concordant to the resection zone than that of the spike imaging ($p<0.001$, Cohen's $d>0.8$). In FIGS. 6A-6B, two examples of individual ESI results of sRipple (left) and spike (right) are shown.

In addition, ESI results were also validated with the SOZ for the patients who had available clinical information. As shown in FIG. 6F-6J, the imaging results of sRipples achieved a LE of around 9.77 ($\pm$5.84) mm comparing to 19.28 ($\pm$7.38) mm of spike imaging ($p<0.01$, Cohen's $d>0.8$). The overlap ratio of sRipples is around 52.75% ($\pm$21.16%) comparing to 32.91% ($\pm$12.46%) of spike imaging, which indicates that the estimated sources of sRipples are more concordant to the SOZ than those of the spikes ($p<0.05$, Cohen's $d>0.8$). Similarly, the SD of sRipples is also significantly better comparing to that of spikes ($p<0.01$, Cohen's $d>0.8$).

The method for the imaging and study of sRipples, in a cohort of 29 focal epilepsy patients with MRE, demonstrated that the scalp recorded sRipples can be adopted as a potential and effective biomarker to delineate the EZ non-invasively. The capability of the method to localize the underlying epileptic brain sources outperformed that of traditionally established spike imaging approach.

In alternative embodiments, the method identifies pHFOs, which are distinctive from the nHFOs (HFAs without consistency on spikes) in various temporal, spectral, and CFC patterns across patients. Moreover, similar discriminability can be demonstrated among subgroups of spikes (i.e., pSpikes, nSpikes, and rSpikes) corresponding to the p/nHFOs with diverse morphological characteristics, where pSpikes are spikes with pHFOs, nSpikes are spikes with nHFOs, and rSpikes are the remaining spikes without any form of concurrent detections. The concurrence between HFOs and spikes not only identifies a subtype of epileptic HFOs but also selects a spike subgroup, which in turn outperforms the conventional spike imaging, suggesting that pHFOs can serve as a discriminator for identifying spikes which are of high significance to determine the EZ.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

Further, the features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof. In particular, one or more features in any of the embodiments described herein may be combined with one or more features from any other embodiments described herein.

Protection may also be sought for any features disclosed in any one or more published documents referred to and/or incorporated by reference in combination with the present disclosure.

What is claimed is:

1. A method of identifying high-frequency oscillation events in EEG data of brain activity, the EEG data scalp-recorded from a plurality of channels, the method comprising:
   eliminating noise from the EEG data by applying a filter to the EEG data;
   segmenting the filtered EEG data into time periods centered around a spike to form data samples segmented by time;
   detecting frequency events in the segmented samples;
   selecting the frequency events that qualify as high frequency oscillations;
   extracting features from the selected frequency events;
   clustering the selected frequency events into a plurality of clusters;
   identifying a putative spike ripple in a cluster of the plurality of clusters;
   extracting a portion of data from the filtered EEG data corresponding to the cluster containing the identified putative spike ripple; and
   projecting brain activity associated with the identified putative spike ripple onto a brain cortex model.

2. The method of claim 1, wherein the noise comprises data generated by at least one of a physiological event and a non-physiological event.

3. The method of claim 2, wherein the physiological event is selected from the group consisting of cardiac pulse, respiration, eye movement, and muscle movement.

4. The method of claim 1, wherein applying a filter comprises:
   applying a high-pass filter above 1 Hz; and
   applying a notch filter at 60 Hz with harmonics using a fast Fourier transform Hann filter with a slope of 2 Hz.

5. The method of claim 1, wherein detecting frequency events in the segmented data samples comprises:
   comparing an amplitude for each segmented data sample to a respective threshold.

6. The method of claim 5, wherein each respective threshold comprises a multiple of a standard deviation of a corresponding amplitude.

7. The method of claim 1, wherein selecting the frequency events that qualify as high frequency oscillations comprises:
   comparing the morphology of each frequency event to a known morphology to identify high frequency oscillations.

8. The method of claim 7, further comprising:
   grouping the selected frequency events from the plurality of channels temporally.

9. The method of claim 1, wherein extracting features from the selected frequency events comprises:
   extracting at least one of time-frequency domain features and spectrogram features.

10. The method of claim 9, wherein the time-frequency domain features are selected from the group consisting of mean, variance, skewness, median frequency, and spectral centroid.

11. The method of claim 9, wherein the spectrogram features are selected from the group consisting of entropy, third-order moment of a histogram, directionality, and block-wise power.

12. The method of claim 1, wherein clustering the selected frequency events comprises:
   estimating the center of a feature distribution; and
   mapping each selected frequency event into one of the plurality of clusters using the expectation-maximization method.

13. The method of claim 12, further comprising:
   evaluating the homogeneity of the spatial and temporal distributions of the selected frequency events in each cluster of the plurality of clusters.

14. The method of claim 13, wherein evaluating the homogeneity is based on the following metrics: a scalp spatial extent and a spike time-locking,
   wherein a potential pathological cluster is selected as the cluster having a minimum mean of the two metrics.

15. The method of claim 1, wherein the EEG data originates from an epileptic brain.

16. The method of claim 1 further comprising:
   modeling the brain activity by equivalent dipoles.

17. The method of claim 1 further comprising:
   modeling the brain activity using a distributed cortical current density model.

18. The method of claim 1, further comprising:
   imaging brain anatomy using a magnetic resonance imaging device; and
   comparing the brain anatomy with the projected brain activity.

* * * * *